United States Patent [19]

Ansell et al.

[11] Patent Number: 5,272,771

[45] Date of Patent: Dec. 28, 1993

[54] GLOVES

[75] Inventors: Christopher W. Ansell, Sawston; Nicholas Medcalf, Ware; Peter W. Williams, Saffron Walden, all of United Kingdom

[73] Assignee: Smith & Nephew plc, England

[21] Appl. No.: 930,480

[22] Filed: Aug. 14, 1992

Related U.S. Application Data

[63] Continuation of Ser. No. 776,653, Oct. 15, 1991, filed as PCT/GB88/00301, Apr. 21, 1988, abandoned, and Ser. No. 424,246, Oct. 17, 1989, Pat. No. 5,088,125.

[30] Foreign Application Priority Data

Apr. 21, 1987 [GB] United Kingdom ............... 8709329
Apr. 28, 1987 [GB] United Kingdom ............... 8710073

[51] Int. Cl.$^5$ ............................................. A41D 19/00
[52] U.S. Cl. ............................................. 2/167; 2/168
[58] Field of Search ................ 2/159, 164, 167, 168, 2/169, 260, 260.1; 427/386; 524/507, 591; 525/454; 528/60

[56] References Cited

U.S. PATENT DOCUMENTS

| | | | |
|---|---|---|---|
| 3,382,138 | 5/1968 | Barth | 2/168 X |
| 3,813,695 | 6/1974 | Podell, Jr. et al. | 2/168 |
| 3,928,271 | 12/1975 | Matsuda et al. | 524/591 |
| 3,971,745 | 7/1976 | Carlson et al. | 525/528 X |
| 3,991,026 | 11/1976 | Matsuda et al. | 524/591 X |
| 4,016,122 | 4/1977 | Matsuda et al. | 525/454 X |
| 4,016,123 | 4/1977 | Matsuda et al. | 524/591 X |
| 4,260,530 | 4/1981 | Reischl et al. | 525/456 X |
| 4,302,852 | 12/1981 | Joung | 2/167 |
| 4,448,922 | 5/1984 | McCartney | 524/501 X |
| 4,463,156 | 7/1984 | McGary, Jr. et al. | 2/168 X |
| 4,548,844 | 10/1985 | Podell et al. | 2/168 X |
| 4,670,330 | 6/1987 | Ishiwata | 2/161 R X |
| 4,755,337 | 7/1988 | Takahashi et al. | 427/386 X |
| 4,777,224 | 10/1988 | Gorzynski et al. | 525/454 |
| 4,857,565 | 8/1989 | Henning et al. | 524/591 X |
| 4,983,662 | 1/1991 | Overbeek et al. | 524/507 X |
| 5,089,205 | 2/1992 | Huang et al. | 2/168 X |

FOREIGN PATENT DOCUMENTS

| | | |
|---|---|---|
| 189773 | 4/1986 | European Pat. Off. |
| 912753 | 12/1962 | United Kingdom |
| 8100345 | 2/1981 | World Int. Prop. O. |

OTHER PUBLICATIONS

Encyclopedia of Polymer Science and Engineering, vol. 13: pp. 277, 292, 293, publ. 1988 by Wiley & Sons Inc.

*Primary Examiner*—William A. Cuchlinski, Jr.
*Assistant Examiner*—Scott W. Cummings
*Attorney, Agent, or Firm*—Rosenman & Colin

[57] ABSTRACT

Gloves, especially those of the type worn by surgeons, and fabricated from elastomeric materials have a hand conducting surface comprising an ionic polyurethane to render the glove hypoallergenic. The surface modifying composition may comprise a blend of an ionic polyurethane and a second polymer, e.g. another polyurethane or an acrylic polymer wherein the particle size of the second polymer are greater than that of the base ionic polyurethane. The use of blends enables donning of the glove to be effected without the aid of donning powder such as starch or talc.

17 Claims, No Drawings

GLOVES

CROSS-REFERENCE

This is a continuation of Ser. No. 776,653 filed Oct. 15, 1991, filed as PCT/GB88/00301, Apr. 21, 1988, now abandoned, and of Ser. No. 424,246 filed Oct. 17, 1989, now U.S. Pat. No. 5,088,125.

This invention relates to gloves and to their manufacture. More particularly, the invention relates to gloves of the type worn by medical practitioners for example those used by surgeons.

Many of the elastomeric materials, for example natural rubber latex, employed for the manufacture of gloves have allergenic properties. Attempts to render such gloves hypoallergenic have included the provision of a laminated inner layer or coating of a less allergenic material. However such layers or coatings suffer problems of delamination or cracking, especially in the regions of flexing or stretching e.g., the knuckles or when the gloves are donned. The problem can be particularly serious if the gloves are donned when the hands are damp.

One method of avoiding delamination is that of U.S. Pat. No. 4,302,852 which discloses a method for bonding two layers wherein an inner glove of a non-allergenic elastomer is covalently bonded to an outer glove of an allergenic elastomer. One suggestion is that polyurethanes with hydroxy groups could be covalently bonded to the allergenic elastomer by use of an isocyanate linker to provide an inner barrier glove of polyurethane. However, the use of agents such as free isocyanates in the manufacture of such gloves could pose a health risk unless considerable care is taken during production.

We have found that hypoallergenic gloves can be produced which have good resistance to delamination and which can be produced without the need to resort to the use of noxious agents such as isocyanates in the glove manufacture. Such gloves are suitable for use by those with sensitive skins.

Gloves fabricated from elastomeric materials such as natural rubber latex have suffered from other problems. For example, they always have been difficult to don due to the high coefficient of friction between the skin and the glove material.

In order to reduce the donning problems it has been conventional practice to employ lubricating agents such as talc or starch. The glove may be 'dusted' with the lubricating agent or donning powder at the time of manufacture and/or at the time of donning. The use of such donning agents has the disadvantage that, if the glove is worn by a surgeon, particles may drop from the glove into the surgical wound possibly resulting in a granuloma. Attempts have been made to eliminate the use of donning powders including treatment of the hand contacting surface of the gloves, for example by halogenating the surface, or by laminating another material having greater lubricity than the base rubber. Laminating the glove, also makes for a more hypoallergenic glove, provided that the integrity of the laminate is maintained.

The integrity of such laminates can be destroyed by either continuous flexing e.g. over the region of the knuckles or stretching e.g. on donning of the glove. Delamination problems can be exacerbated if the gloves are donned whilst the hands are wet, a practice which is increasing, particularly in the United States of America.

One method of providing a laminate structure reported, for reducing the friction between the glove and the user's hand, is that disclosed in U.S. Pat. No. 3,813,695 wherein a hydrogel resin is polymerised onto a rubber surface in order to improve the interface bond. Such hydrophilic materials are also stated to have the capacity to absorb perspiration or other lubricating materials such as a silicone lubricant.

The present invention further seeks to provide a glove wherein good donning characteristics are obtained without the need for donning agents such as talc and without the need to produce an inner laminar by polymerisation methods.

According to an aspect of the present invention there is provided a hypoallergenic glove fabricated from an allergenic elastomer, characterised in that the hand contacting surface of the glove has been modified by an ionic polyurethane.

According to a further aspect of the invention there is provided a glove fabricated from a first flexible elastomeric material, characterised in that the hand contacting surface of the glove has been coated with a second elastomeric material comprising a blend of an ionic polyurethane and a second polymer having a particle size greater than that of the ionic polyurethane.

The ionic polyurethanes employed for the present invention are preferably anionic in nature and may have a typical charge density ranging from 20 to 50 m eq, per 100 gm of solids. To avoid wet delamination problems it is preferred to employ polyurethanes having a charge density of greater than 30 m e.g. per 100 gm of solids.

Preferred polyurethanes used for the present invention comprise the reaction product of urethane prepolymer and an ionic chain extender having at least one group which is reactive with isocyanate groups and at least one salt-type group.

Suitably the ionic chain extender is an alkali metal, e.g., sodium, salts of either an N-($\omega$-aminoalkyl)-$\omega^1$-amino alkyl sulphonic acid or an amino carboxylic acid.

Specific examples of such ionic chain extenders include the sodium salt of 2[(2-aminoethyl)amino]ethane sulphonic acid and sodium lysinate.

The urethane prepolymers employed in the present invention are typically formed by reaction between a polyol, preferably a linear polyol having a molecular weight of not more than about 2000 and a poly functional isocyanate, preferably a monomeric isocyanate.

It is highly desirable for the soft block components of the polymer to be essentially hydrophobic in nature. Accordingly, preferred polyols are $\alpha,\omega$-dihydroxy polyesters e.g., esters formed from alkane diols and adipic acid. However, other soft block variations include polycaprolactones, polyethers or polyalkylsiloxanes, all preferably having formula weights of not more than about 2000.

The isocyanate component employed for the prepolymer formation should contain at least two functional groups of sufficiently high activity for the ionic chain extender (and any other chain extending amine) to successfully compete with water in reactions at the isocyanate termini of the extended prepolymer and at a sufficient rate for the ionic groups to become incorporated into the polymer within a short time of their addition.

The isocyanate may be an aliphatic or aromatic isocyanate. Suitable aliphatic isocyanates include hexamethylene- and trimethylhexamethylene diisocyanates. More preferred are aromatic isocyanates such as diphenylmethane-4,4'-diisocyanate.

In addition to the use of an ionic chain extender, other extenders may be employed e.g. diols or diamines. Thus, for example the prepolymer may be reacted in the presence of a catalyst with a diol chain extender, e.g., butane-1,4-diol and thereafter reacting the extended prepolymer with a mixture comprising an ionic chain extender, as hereinbefore defined, and, optionally, another amine chain extender such as ethylenediamine or an alkyldiamine.

Where the ionic polyurethane alone is used as the coating, to render, the hand contacting surface hypoallergenic, the polyurethane may be applied as a dispersion, typically containing from 2 to 20% by weight solids, preferably 3 to 10% and more preferably 4 to 6%, by weight solids. The casting thickness obtained from such dispersions may be up to 50 μmm. Preferably, the thickness of uninterrupted casting will be up to 20 μmm, more preferably from 1 to 5 μmm.

The anionic polyurethane is fully reacted prior to contact with the allergenic elastomer and is not bonded thereto by means of any co-valent bonds. The bonding of the polyurethane is believed to be brought about by hydrophobic interaction between the polyurethane and the allergenic elastomer.

Thus accordance with an embodiment of the first aspect of the invention hypoallergenic gloves are prepared by a process including the steps of contacting a preformed glove, fabricated from an allergenic elastomer, with an aqueous dispersion of an ionic polyurethane.

The preformed allergenic elastomeric glove may be fabricated by conventional techniques. Thus, for example, a suitably shaped former is pretreated by application of a coagulant for the allergenic elastomer, after which the former is dipped into a emulsion of the allergenic elastomer. Preferably the allergenic elastomer is a rubber latex preferably a natural rubber latex. Synthetic rubbers may also be used. The dipping process typically produces a glove having a final thickness of for 150 to 200 μm. After a leaching treatment to remove any water soluble components, the allergenic elastomer-coated formed is then overdipped in an aqueous dispersion of the ionic, e.g. anionic, polyurethane and cured according to known techniques.

When blend of polymer is applied to provide improved donning properties, the second polymer should be present as particles of greater size than that of the first or base polymer, i.e. ionic polyurethane. Typically the base ionic polyurethane will have a particle size of less than 1 μm, preferably from 0.5 to 1.0 μm most preferably about 200 nm. The particle size of the second polymer will be up to 2.0 μm or greater, typically from 1.5 to 2.0 μm.

It is desirable for the blend to contain a greater proportion of the base ionic polyurethane. Thus the blend may contain greater than 50% by weight of the ionic polyurethane and preferably more than 60% by weight of the base ionic polyurethane most preferably about 70%.

The polymer blend is preferably applied to the glove, fabricated from the first elastomeric material, as a coating. The coating composition may be an aqueous dispersion or latex containing the polymers as the disperse phase and water is the transport phase.

The polymer blend dispersions or latices may typically contain from 1 to 20% by weight solids, preferably 1 to 10% and more preferably 1 to 5% by weight solids. The coating thickness obtained from such dispersions may be upto 50 μm. Preferably, the thickness of coating will be upto 20 μm, more preferably from about 1-5 μm. However, agglomerates of the second polymer may increase the total thickness locally by a factor of upto two for example a coating of about 5 μm may have total high spots upto about 10 μm.

The second polymer may be any polymer which is compatible with the base ionic polyurethane, at least when the blend is finally formulated. Desirably formulations or compositions containing the base polymers should be compatible or reversible to avoid blending problems.

Suitable second polymers include other polyurethanes preferably ionic polyurethanes having the same charge identity as the base ionic polyurethane, the polymer blend may therefore be a mixture of two ionic polyurethanes of differing particle sizes.

Other suitable second polymers include polymers and copolymers derived from acrylic or methacrylic acid and esters thereof. Suitable second polymers of this class are methacrylate copolymers such as copolymers of ethoxy-ethylmethacrylate (EEMA) and methoxy ethylmethacrylate (MEMA).

In order to ensure compatibility between the acrylic latices and the ionic polyurethane dispersion it is preferred to incorporate a surfactant into the copolymer latex. The surfactant is itself, preferably copolymerisable. An apt surfactant is one having the formula

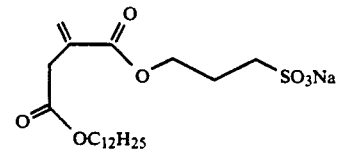

such a surfactant may comprise upto 10% preferably upto 5% by weight of the total polymer.

The hardness of the final polymer can be altered by incorporating a monomeric acrylic species of higher glass transition temperature (Tg) than that of the base monomers. Suitable hardness modifiers include 2-hydroxyethylmethacrylate (HEMA), methylmethacrylate (MMA) and acrylic acid (AA). The hardness modifiers may be present in amounts upto 20%, preferably upto 15% by weight of the final composition.

In a preferred embodiment, the combined amounts of surfactant and hardness modifier should not exceed 20% by weight of the final acrylic polymer.

The acrylic latices employed in the present invention may be prepared by emulsion polymerisation techniques. Thus the monomeric reactants, including surfactant may be first emulsified in water and thereafter reacted whilst heating in the presence of a free radical catalyst such as ammonium persulphate.

The polymer blends employed in the present invention may be applied as a coating from an aqueous dispersion thereof by conventional techniques.

The polymer blends are preferably applied to the glove material from an aqueous dispersion containing up to 10%, more preferably upto 5% by weight of total solids. A suitable blend would be a 70:30 aqueous 5% dispersion of two anionic polyurethanes having particle sizes of respectively upto 1.0 μm and up to 2.0 μm.

Accordingly the present invention further provides a process for the manufacture of gloves, such as those worn by surgeons including the steps of contacting a preformed glove fabricated from an elastomeric material, with an aqueous dispersion comprising a blend of an ionic polyurethane and a second polymer having a particle size greater than that of the ionic polyurethane.

The preformed elastomeric glove may be fabricated by conventional techniques. Thus, typically a suitably shaped former is pretreated by application of a coagulant for the elastomer, e.g. a natural rubber latex after which the former is dipped into a emulsion of the elastomer. The dipping process typically produces a glove having a final thickness of for 150 to 180 $\mu$m. After a leaching treatment to remove any water soluble components, elastomer-coated former is then overdipped in an aqueous dispersion of the polymer blend and cured according to known techniques.

Prior to coating with the polymer blend dispersion the coated former may be first coated with a tie coat which may comprise the ionic polyurethane. Thus after the leaching treatment, the coated former may be dipped into a dispersion of an ionic polyurethane, preferably having the same charge sign as that of the polyurethane employed in the polymer blend. After drying the tie-coated former may then be overdipped in the blend dispersion and cured.

For totally powder-free gloves it is desirable to replace the talc or starch conventionally used in coagulant sections with a polymer comprising the ionic polyurethane employed in the present invention. The polyurethane may be one suitable for use as the ionic polyurethane component of the blend or a polyurethane employed as the second polymer component of the blend.

The invention will be illustrated by the following Examples.

EXAMPLE 1

A linear $\alpha$-$\omega$-dihydroxy copolyester prepared by reacting adipic acid with hexane-1,6-diol, and sold under the trade name "Diorex 785" was taken and 138 g of the polyester was dried under vacuum at 120° C. for 30 minutes in a reaction vessel. The temperature of the polyester was lowered to 100° C., and 52.6 gms of 4,4'-diisocyanatetodiphenylmethane was added to the reaction vessel. The pressure in the reaction vessel was maintained at 1 bar in an atmosphere of nitrogen. The ester/isocyanate mixture was stirred for 15 minutes, after which 150 ml of THF, 4.0 gm of butane-1,4-diol and 0.1 gm of di-n-butyltindilaurate were consecutively added at atmospheric pressure ($N_2$) and the reaction mass stirred at reflux under nitrogen for one hour. At the end of this period, 450 ml of THF was added and the reaction product allowed to cool to room temperature.

With high-shear stirring the following reactants were added consecutively to the reaction vessel:
(i) 73 mls of 1.6 w/v solution of ethylenediamine in acetone;
(ii) 19.46 ml of 2M sodium lysinate
(iii) 19.46 ml of 2M aqueous solution of sodium taurine.

Water (800 mls) was then added with continued high shear mixing followed by vacuum distillation of the THF. The residue was a stable white coloured dispersion having a mean particle size of about 120 nm. A sample of the dispersion was spread and allowed to dry to form a firm inextensible film having the following properties:

Tg (onset): $-49°$ to $-38°$ C.
Water uptake (based on hydratd polymer): 23%
Charge density: 40 m eq/100 gm.

The solids content of the remaining aqueous dispersion was adjusted to 5% by weight.

Glove manufacture

A coagulant solution was prepared consisting of:
$Ca(NO_3)_2$—12.02%
$Zn(NO_3)_2$—5.29%
Talc—3.85%
Lactic Acid—3.85%
Ethanol—67.4%
Methanol—7.5%
and into this solution was dipped a glove former preheated to about 112° C. After removal of the former from the coagulant solution, it was air-dried for about 2 minutes and then immersed ina pre-vulcanised natural rubber latex. The latex coated former was then withdrawn, air-dried for about 2 minutes and immersed in a leach tank of water at about 70° C. for 2 minutes to extract any water-soluble materials. Following withdrawal from the leaching tank the coated former was overdipped in the 5% aqueous dispersion of anionic polyurethane. The residence period was about 20 seconds. After removal from the overdip dispersion the coated former was placed in a curing oven at 115° C. for 30 minutes and thereafter removed from the curing oven.

EXAMPLES 2-4

The procedure of Example 1 was repeated except that the ratio of ionic diamine to nonionic diamine was altered. In each case the ionic amine was sodium2-[2-aminoethyl)amino]ethane sulphanate (AEAES) and the non-ionic amine chain extended was ethylene diamine (ED).

The following table reports the changes in water uptake (% in hydrated film) and film Glass Transition (onset) point (Tg).

| Overall Change | Example | | |
|---|---|---|---|
| | 2 | 3 | 4 |
| (m eg/100 g) | 20 | 30 | 40 |
| ED (mls) | 219 | 146 | 73 |
| AEAES (mls) | 0 | 7.39 | 14.77 |
| Total Amine (moles) | 0.0584 | 0.0584 | 0.0584 |
| TG (°C.) | — | −52 to −32 | −43 to −30 |
| Approx. Water Uptake (%) | 8 | 25 | 44 |

EXAMPLE 5

(a) An ionic polyurethane was prepared as described in Example 1.

(b) An acrylic latex was prepared in the following manner

Into a reaction vessel was added 70 parts by weight of ethoxyethylmethacrylate (EEMA), 30 parts by weight methodyethylmethacrylate and surfactant (0.4 parts by weight). Water was added to provide a ratio of non-aqueous components to water of about 1:1. The reactants were emulsified under high shear and over a period of 1 hour the emulsion was gradually added to a 10% aqueous solution of ammonium persulphate, preheated to 85° C.

The admixture was maintained under an insert atmosphere ($CO_2$) at 85° C. for a further 1.25 hours.

At the end of the reaction period the mixture was cooled and filtered. The solids content of the final latex was 40% w/w.

The ionic polyurethane dispersion and acrylic latex were then blended to give an aqueous dispersion having a polymer ratio of 70 parts polyurethane to 30 parts acrylic polymer and the solids content adjusted to 5% by weight.

Gloves were manufactured in the manner described in Example 1 except that following withdrawal from the leaching tank the coated former was overdipped in th 5% aqueous dispersion of the polymer blend. The residence period was about 20 seconds. After removal from the overdip dispersion the coated former was placed in a curing oven at 115° C. for 30 minutes and, after removal from the curing oven, the glove was stripped from the former a portion of the glove was taken and examined by scanning electron microscopy. It was observed that the surface consists of irregularly shaped cluster of particles with an average principal dimension of about 80 $\mu$mm. The average distance between the clusters is about 60 $\mu$m. Within the cluster the average particle size was observed to be about 0.6 $\mu$m and the interparticle separation about 0.9 $\mu$mm. Gloves were also subjected to physical tests to determine the ease of donning compared with conventional talc dusted gloves, on a scale of A (talc treated latex) to F (untreated latex), the gloves in accordance with the invention were graded B.

EXAMPLE 6

An anionic polyurethane was prepared as described in Example 1 except that sodium 2-[2-aminoethyl-)amino]ethane sulphonate was used instead of lysine as the ionic chain extender.

A polymer blend was prepared by taking the aqueous anionic polyurethane and blending it with a second anionic polyurethane dispersion. The second material had particle size distribution of from 1 to 1.5 $\mu$m and was a polyester polyurethane with a 1,6-hexanediol/phthalic acid soft block containing an alkyl phenol polyether non-ionic surfactant. The second dispersion had a solids content of 56.8% w/w.

The two polyurethanes were blended to a polyurethane (ionic) to polyurethane (second) ratio of 70:30 and the solids concentration of blend was adjusted to 5% by weight.

The procedure described in Example 5 was followed to produce gloves to have comparable donning qualities to those of the polyurethane/acrylate glove described in Example 5.

We claim:

1. A glove fabricated from an allergenic elastomer wherein the hand contacting surface of the glove has been modified by an ionic polyurethane containing fully reacted isocyanate groups to render the glove hypoallergenic, wherein said ionic polyurethane comprises a blend derived from a particulate ionic polyurethane and a second particulate polymer having a particle size greater than that of the ionic polyurethane.

2. A glove as claimed in claim 1 which is fabricated from natural rubber.

3. A glove as claimed in claim 1 wherein the ionic polyurethane a blend thereof is present on the hand-contacting surface of the glove at a thickness of from about 1 to 5 $\mu$m.

4. A glove as claimed in claim 1 wherein the ionic polyurethane is an anionic polyurethane.

5. A glove as claimed in claim 1 wherein the ionic polyurethane is the reaction of a urethane prepolymer and an ionic chain extender having at least one group which will react with isocyanate groups and at least one salt-type group.

6. A glove as claimed in claim 5 wherein the ionic chain extender is an alkali metal of either an N-($\omega$-aminoalkyl)-$\omega^1$-amino alkyl sulphonic acid or an aminocarboxyl acid.

7. A glove as claimed in claim 6 wherein the ionic chain extender is the sodium salt of either 2[(2-aminoethyl)amino] ethane sulphonic acid either or lysine.

8. A glove as claimed in claim 5 in which the urethane prepolymer is the reaction product of a polyol having a molecular weight of not more than about 2000 and a polyfunctional isocyanate.

9. A glove as claimed in claim 5 wherein the ionic polyurethane contains a chain extender in addition to the ionic chain extender.

10. A glove as claimed in claim 5 wherein the polyol is an $\alpha,\omega$-dihydroxy polyester.

11. A glove as claimed in any one of claim 1 wherein the polymer blend contains at least 50% of the ionic polyurethane.

12. A glove as claimed in claim 1 wherein the second polymer is a polyurethane.

13. A glove as claimed in claim 12 wherein the polyurethane is an ionic polyurethane having the same charge identity as the base ionic polyurethane.

14. A glove as claimed in claim 1 wherein the second polymer is a polymer or copolymer derived from acrylic or methacrylic acid or esters thereof.

15. A glove as claimed in claim 14 wherein the second polymer in the form of a latex containing a copolymerisable surfactant.

16. A glove as claimed in claim 1 wherein the blend is a 5% by weight solids aqueous dispersion of two anionic polyurethanes in a weight ratio of about 70% of a first anionic polyurethane having a particle size up to 1.0$\mu$ to 30% of a second anionic polyurethane having a particle size up to 2.0$\mu$ and particles larger than the particles of the first anionic polyurethane.

17. A glove fabricated from a first flexible elastomeric material, characterised in that the hand contacting surface of the glove has been coated with a second elastomeric material comprising a blend of an ionic polyurethane and a second polymer having a particle size greater than that of the ionic polyurethane.

* * * * *